United States Patent
Coyle et al.

(10) Patent No.: US 6,966,890 B2
(45) Date of Patent: Nov. 22, 2005

(54) CONVERTIBLE BALLOON CATHETER AND MANUFACTURE THEREOF

(75) Inventors: Noel Coyle, Galway (IE); Niall Duffy, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 445 days.

(21) Appl. No.: 10/226,117

(22) Filed: Aug. 23, 2002

(65) Prior Publication Data

US 2004/0039409 A1    Feb. 26, 2004

(51) Int. Cl.$^7$ ........................ A61M 25/10; A61M 29/00
(52) U.S. Cl. ................................. 604/103.04; 606/194
(58) Field of Search ...................... 604/103.04–103.08; 606/103.04–103.08

(56) References Cited

U.S. PATENT DOCUMENTS

| | | | |
|---|---|---|---|
| 4,748,982 A | 6/1988 | Horzewski et al. | |
| 4,762,129 A | 8/1988 | Bonzel | |
| 4,988,356 A | 1/1991 | Crittenden et al. | |
| 5,040,548 A | 8/1991 | Yock | |
| 5,061,273 A | 10/1991 | Yock | |
| 5,149,330 A | 9/1992 | Brightbill | |
| 5,171,222 A | 12/1992 | Euteneuer et al. | |
| 5,178,158 A | 1/1993 | de Toledo | |
| 5,205,822 A | 4/1993 | Johnson et al. | |
| 5,217,435 A | 6/1993 | Kring | |
| 5,263,932 A | 11/1993 | Jang | |
| 5,290,241 A | 3/1994 | Kraus et al. | |
| 5,300,085 A | 4/1994 | Yock | |
| 5,318,532 A * | 6/1994 | Frassica | ............... 604/97.01 |
| 5,324,269 A | 6/1994 | Miraki | |
| 5,327,885 A | 7/1994 | Griffith | |
| 5,334,187 A | 8/1994 | Fischell et al. | |
| 5,336,184 A | 8/1994 | Teirstein | |
| 5,350,395 A | 9/1994 | Yock | |
| 5,357,978 A | 10/1994 | Turk | |
| 5,364,376 A * | 11/1994 | Horzewski et al. | ......... 604/528 |
| 5,387,226 A | 2/1995 | Miraki | |
| 5,389,087 A | 2/1995 | Miraki | |
| 5,409,459 A | 4/1995 | Gambale | |
| 5,451,233 A | 9/1995 | Yock | |
| 5,458,639 A | 10/1995 | Tsukashima et al. | |
| 5,460,185 A | 10/1995 | Johnson et al. | |
| 5,466,222 A | 11/1995 | Ressemann et al. | |
| 5,489,271 A | 2/1996 | Andersen | |
| 5,496,346 A | 3/1996 | Horzewski et al. | |
| 5,501,227 A | 3/1996 | Yock | |
| 5,531,700 A | 7/1996 | Moore et al. | |
| 5,549,556 A | 8/1996 | Ndondo-Lay et al. | |

(Continued)

FOREIGN PATENT DOCUMENTS

EP    0 518 205 B1    8/1996

(Continued)

*Primary Examiner*—Anhtuan T. Nguyen
*Assistant Examiner*—E Houston

(57) ABSTRACT

A convertible balloon catheter for use as either an over-the-wire catheter or a rapid exchange catheter, comprising a flexible outer shaft, flexible inner shaft, angioplasty balloon, and bifurcate hub. The inner shaft is comprised of a relatively elastic, deformable material and forms an inflation lumen. The inner inflation shaft is attached to the outer shaft, and has a cross section that is radially collapsible to increase the size of a full-length guide wire lumen formed between an outer surface of the inner shaft and an inner surface of the outer shaft. Formed in the outer shaft is a hatch, which covers a guide wire port. The hatch has a perforated peripheral edge which allows the hatch to be removed. The balloon is simply constructed with essentially four components, which significantly reduces the labor required for assembly.

2 Claims, 3 Drawing Sheets

U.S. PATENT DOCUMENTS

| | | | |
|---|---|---|---|
| 5,554,118 A * | 9/1996 | Jang | 604/102.02 |
| 5,571,094 A | 11/1996 | Sirhan | |
| 5,578,009 A | 11/1996 | Kraus et al. | |
| 5,624,281 A | 4/1997 | Christensson | |
| 5,626,600 A | 5/1997 | Horzewski et al. | |
| 5,685,312 A | 11/1997 | Yock | |
| 5,718,680 A | 2/1998 | Kraus et al. | |
| 5,749,888 A | 5/1998 | Yock | |
| 5,755,685 A | 5/1998 | Andersen | |
| 5,769,868 A | 6/1998 | Yock | |
| 5,779,671 A | 7/1998 | Ressemann et al. | |
| 5,807,355 A | 9/1998 | Ramzipoor et al. | |
| 5,919,164 A | 7/1999 | Andersen | |
| 5,919,175 A | 7/1999 | Sirhan | |
| 5,921,971 A | 7/1999 | Agro et al. | |
| 5,944,562 A | 8/1999 | Christensson | |
| 5,947,925 A | 9/1999 | Ashiya et al. | |
| 5,947,927 A | 9/1999 | Mertens | |
| 6,013,068 A | 1/2000 | Spiegelhalter | |
| 6,036,715 A | 3/2000 | Yock | |
| 6,056,719 A | 5/2000 | Mickley | |
| 6,096,009 A | 8/2000 | Windheuser et al. | |
| RE36,857 E | 9/2000 | Euteneuer et al. | |
| 6,152,910 A | 11/2000 | Agro et al. | |
| 6,165,197 A | 12/2000 | Yock | |
| 6,475,187 B1 * | 11/2002 | Gerberding | 604/102.02 |

FOREIGN PATENT DOCUMENTS

| | | |
|---|---|---|
| WO | WO 92/17236 | 10/1992 |
| WO | WO 92/20397 | 11/1992 |
| WO | WO 93/11822 | 6/1993 |

* cited by examiner

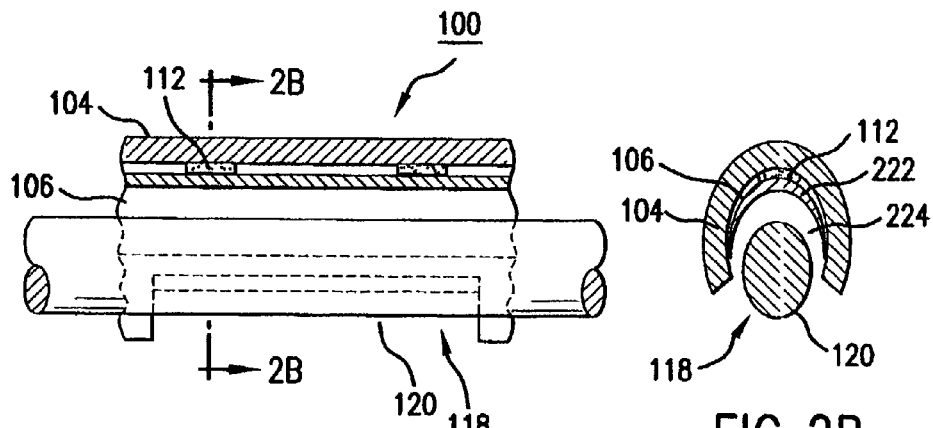
FIG. 2A
FIG. 2B
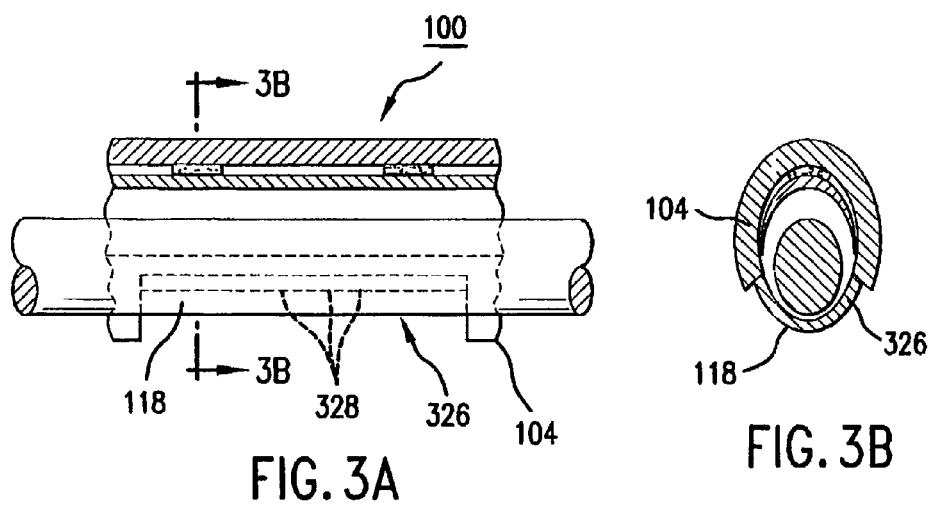
FIG. 3A
FIG. 3B
FIG. 4A
FIG. 4B

CONVERTIBLE BALLOON CATHETER AND MANUFACTURE THEREOF

BACKGROUND OF THE INVENTION

1. Field of the Invention

This invention relates generally to a medical device. More specifically, the invention relates to a balloon catheter that is convertible from an over-the-wire catheter (OTW) to a rapid-exchange (RX) catheter.

2. Background of the Invention

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen. The wall of the artery itself is also stretched when the balloon is inflated.

One or multiple dilations may be necessary to effectively dilate the artery. In many instances, successive dilations using a succession of balloon catheters with balloons of increasingly larger diameters may be required. In order to accomplish the multiple dilations, the original catheter must be removed and a second balloon catheter tracked to the lesion.

There are several types of catheters presently available for performing the above-mentioned procedure. The two types of catheters most often used are referred to as over-the-wire (OTW) catheters and rapid exchange (RX) catheters. An OTW catheter has a guide wire lumen, which runs the entire length of the catheter. A RX catheter, on the other hand, has a guide wire lumen that runs for only the distalmost portion of the catheter.

To remove an OTW catheter, an extension must be placed on the original guide wire and multiple operators are required to hold the extended guide wire in place while the original catheter is changed out.

A RX catheter avoids the need for multiple operators when changing out the catheter and therefore is often referred to as a "single operator" catheter. With a rapid exchange catheter, the guide wire is outside the shaft of the catheter for all but the distalmost portion of the catheter. The guide wire can be held in place without an extension when the catheter is removed from the body. Once the original catheter is removed, a subsequent RX catheter may be threaded onto the in-place guide wire and tracked to the lesion.

However, there are instances when the guide wire and not the catheter must be replaced. For example, the guide wire may become damaged during the procedure or it may be discovered during the procedure that a different shape, length, or size of guide wire is needed. An OTW catheter, with the guide wire lumen extending the entire length of the catheter, allows for simple guide wire exchange. With a RX catheter, the guide wire lumen does not extend the entire length of the catheter. Therefore, the guide wire, and most of the catheter, must be removed from the body in order to exchange guide wires. Essentially the procedure must then start anew because both the guide wire and the catheter must be retracked to the lesion.

The choice of whether an OTW or RX catheter is best for a given procedure often depends upon the specifics of the procedure and often arises in real time of the procedure. For example, if a procedure requires multiple balloons to effectuate proper dilation, a RX catheter, allowing easy exchange of catheters, would be the preferred choice. But, if a procedure requires a change of guide wires, which in clinical practice is common, an OTW catheter is particularly advantageous because it gives a practitioner the ability to do so without changing catheters. Therefore, a balloon catheter capable of use as both an OTW and a RX catheter within the same procedure is particularly advantageous.

There are existing catheters that disclose universal mode designs, i.e., a design for use as either an OTW or RX catheter. For instance, an OTW catheter has been designed with a means for removing the catheter without the need for an extension to the guide wire. Essentially, a slit the length of the outer shaft of the catheter allows an operator to remove the guide wire from the catheter by holding the guide wire in place, and "peeling away" the catheter as the guide wire moves through the slit thereof.

However, this design does not allow the catheter to be used as both a RX catheter and an OTW catheter because by tearing away the catheter outer wall to expose the guide wire inside, the catheter is essentially destroyed. Back loading a subsequent guide wire once the catheter outer wall has been peeled away would be difficult if not impossible because the outer wall would no longer contain the guide wire.

Additionally, a catheter designed to eliminate the need for guide wire extensions or exchange wires is disclosed in U.S. Pat. No. 4,988,356, incorporated herein by reference (Crittenden, et al.). This "zipper-type" catheter includes a catheter shaft having a cut that extends longitudinally between the proximal end and the distal end of the catheter and that extends radially from the catheter shaft outer surface to the guide wire lumen. A guide member slidably coupled to the catheter shaft functions to open the cut such that the guide wire may extend transversely into or out of the cut at any location along its length. By moving the guide member, the effective over-the-wire length of the zipper-type catheter is adjustable.

When using the zipper-type catheter, the guide wire is maneuvered through the patient's vascular system such that the distal end of the guide wire is positioned across the treatment site. With the guide member positioned near the distal end of the catheter, the proximal end of the guide wire is threaded into the guide wire lumen opening at the distal end of the catheter and through the guide member such that the proximal end of the guide wire protrudes out the proximal end of the guide wire member. By securing the guide member and the proximal end of the guide wire in a fixed position, the catheter may then be transported over the guide wire by advancing the catheter toward the guide member. In doing so, the catheter advances through the guide member such that the guide wire lumen envelops the guide wire as the catheter is advanced into the patient's vasculature. In a PTCA embodiment, the zipper-type catheter may be advanced over the guide wire in this manner until the distal end of the catheter having the dilatation balloon is positioned within the stenosis and essentially the entire length of the guide wire is encompassed within the guide wire lumen.

Furthermore, the indwelling zipper-type catheter may be exchanged with another catheter by reversing the operation described above. To this end, the indwelling catheter may be removed by withdrawing the proximal end of the catheter from the patient while holding the proximal end of the guide wire and the guide member in a fixed position. When the catheter has been withdrawn to the point where the distal end of the cut has reached the guide member, the distal portion of the catheter over the guide wire is of a sufficiently short length that the catheter may be drawn over the proximal end of the guide wire without releasing control of the guide wire or disturbing its position within the patient. After the catheter has been removed, another catheter of any type may be threaded onto the guide wire and advanced over the guide wire in the same manner described above with regard to the zipper-type catheter. The zipper-type catheter not only permits catheter exchange without the use of the very long exchange guide wire and without requiring withdrawal of the initially placed guide wire, but it also overcomes many of the other difficulties discussed in association with RX catheters.

Despite these advantages, original zipper-type catheters in accordance with U.S. Pat. No. 4,988,356 at times fail to adequately contain the guide wire within the guide wire lumen during normal operation. In particular, as the catheter was advanced over the guide wire, the catheter could bend or buckle such that the guide wire could protrude from the catheter shaft. If the guide wire protruded from the catheter shaft, it could subsequently become pinched, and the distal end of the guide wire could be pulled out of or pushed beyond the treatment site, thus complicating the procedure and requiring repositioning within the patient's vasculature. Bending or buckling of a zipper-type catheter could also occur proximal to the guide member, where the guide wire is absent from the guide wire lumen. Thus there arises the need for a balloon catheter that gives a practitioner the flexibility to use the catheter as both an OTW and/or a RX catheter within the same procedure. It is among the general objects of the invention to provide an improved device that overcomes the foregoing difficulties.

The convertible balloon catheter of the present invention, capable of use as an OTW and a RX catheter, is a dual lumen catheter and as such, contains both a full-length guide wire lumen and an inflation lumen. The guide wire lumen must be large enough to allow the guide wire to pass through unimpeded. However, the guide wire lumen can not be so sized that the dual lumen catheter results in an unacceptable increase in the outer diameter of the catheter shaft. There arises a need to maintain a small overall outer diameter for the convertible catheter but not decrease the size of the guide wire lumen to the point that resistance between the catheter and the guide wire is adversely affected. The convertible catheter of the present invention includes a collapsible inflation lumen, which can be any shape, for example crescent-shaped, "D"-shaped, or circular. During insertion of the guide wire into the guide wire lumen, the inflation lumen is collapsible which allows for an increase in the dimensions of the guide wire lumen. The enlarged guide wire lumen eases tracking of the catheter over the guide wire.

Assembling balloon catheters is a process that requires the intricate steps of attaching the various parts of the catheters. Each component of the catheter is attached to the others by hand, often in an assembly-line type setting. The components of angioplasty catheters are relatively small and not easily attached to the others. Tack welding and glueing the component parts can be a very difficult task. Each step presents the chance that human error will lead to a faulty product. Thus there arises the need to minimize the number of components of the balloon catheter to minimize the number of steps necessary to assemble the catheter.

For the present invention, the general method of manufacture could be as follows: an extruded, or blown, thin-walled tube (inner shaft) is placed into, for example, a discretely extruded tapered shaft (outer shaft). Using a CO laser, for example, the inner shaft is tack welded to the inner surface of the outer shaft. A much longer tack weld is applied at the distal-most end of the inner shaft after which one or more small holes are formed through the outer shaft, tack weld, and inner shaft. Again the holes are formed by laser or another method, to allow access from the inflation lumen to the balloon. The balloon can be positioned onto the distal-most portion of the outer shaft and laser-welded, glued or attached via a suitable method. The distal-most tip of the catheter can be profiled either mechanically, e.g., sanding, by laser or another suitable heating method. The removable hatch is formed by creating a multitude of small, relatively weak points or preforations in a predetermined pattern at one or more locations in the outer shaft. At the proximal end of the catheter, a molded hub can be for example over-molded or ultrasonically welded onto the shaft assembly.

Accordingly, there is a need for a convertible catheter that can be used as either an OTW or RX catheter, a convertible catheter with a reduced outer diameter, and a simplified method of manufacture.

SUMMARY OF THE INVENTION

To achieve the foregoing and other objects, and in accordance with the purposes of the present invention as embodied and broadly described herein, the angioplasty balloon catheter of the present invention provides a balloon catheter capable of being used as both an over-the-wire and a rapid exchange catheter. The balloon catheter has a simplified construction, essentially comprised of a hub, a dual lumen shaft, and an angioplasty balloon.

In the present invention, the balloon catheter has a flexible outer shaft, which has an outer surface, an inner surface, a proximal end, and a distal end. Additionally, the balloon catheter has a flexible inner shaft that has an inner surface, and an outer surface, a proximal end, and a distal end. The inner shaft is slidably inserted into the outer shaft and the outer surface of the inner shaft is connected by tack welds to the inner surface of the outer shaft. The flexible inner shaft forms an inflation lumen of the balloon catheter, and a space between the outer surface of the inner shaft and the inner surface of the outer shaft forms a guide wire lumen.

Further, at the distal end of the catheter, a balloon is attached to the outer surface of the outer shaft. The balloon can be of any shape or size commonly used in angioplasty procedures. The dual lumen shaft has inflation ports to allow fluid communication between the inflation lumen and the balloon so that the fluid introduced via the hub passes through the inflation lumen and into the balloon, thereby inflating it.

Additionally, the flexible inner shaft is thin-walled and has for example a crescent-shaped, "D"-shaped, or circular cross section, and is preferably made of a relatively elastic, deformable material similar to a material used for an angioplasty balloon. The flexible inner shaft is attached to the hub at its proximal end and is hermetically sealed at its distal end. When not filled with inflation fluid, the inner shaft is radially collapsible such that its cross-section substantially conforms to the shape of the inner surface of the outer shaft.

Thus when the inner shaft is collapsed, the guide wire lumen is enlarged, thereby facilitating tracking of the catheter over the guide wire.

In order to convert the catheter of the present invention from OTW use to RX use, a removable hatch is formed in a distal portion of the outer shaft proximal of the balloon. The hatch is formed by creating perforations through the outer shaft in any appropriate form, such as a rectangle. The hatch, when removed, forms a guide wire port and is only large enough to allow for the guide wire to pass through. The outer surface of the hatch can be recessed from, flush with, or protruding from the outer surface of the outer shaft in which it is formed.

In an alternate embodiment, the outer shaft may include a slot cut through a distal portion thereof proximal of the balloon, for example about 25 cm from a distal tip of the catheter. The slot, which forms a guide wire port, is orientated along the shaft's axis and is any appropriate form, such as rectangular. The slot is large enough to accommodate entry and exit of the guide wire, but does not run the entire length of the catheter.

Finally, a bifurcate hub is attached to the proximal end of the outer shaft. A guide wire hub of the bifurcate hub communicates with the guide wire lumen of the dual lumen shaft and an inflation hub of the bifurcate hub fluidly communicates with the inflation lumen of the dual lumen shaft. The guide wire hub attached to the guide wire lumen facilitates insertion of the guide wire into the catheter and the inflation hub attached to the inflation lumen facilitates introduction of the inflation fluid used to expand the balloon.

Further, the present invention provides a simplified method of manufacturing a convertible balloon catheter. The method includes obtaining a flexible first tube and a flexible second tube. The second tube is radially smaller than the first tube and slidably fits within the first tube. The second tube's distal end is hermetically sealed by any one of many well known methods in the art. Once sealed, the second tube is slidably placed inside the first tube and attached to it, by for example, tack welding the second, smaller tube's outer surface to the inner surface of the first tube. Inflation ports are made in a distal portion of the dual lumen shaft, which allow inflation fluid from the inflation lumen to be in fluid communication with the balloon. The inflation ports are cut in the shafts using a laser, for example. A balloon is attached to the outer surface of the distal end of the first tube in such a location that it is in fluid communication with the inflation fluid via the inflation ports. The balloon is either glued or welded to the distal end of the first tube. A bifurcate hub is attached to the proximal ends of the outer shaft and the inner shaft by any one of the well known methods in the art of bonding or welding together catheter components, for example laser welded or ultrasonically welded.

During manufacture of the first tube, a hatch is formed for example by molding a recess in the outer surface of the tube. Once the recess is formed, a perforated edge is cut around the edge of the recess and through the outer shaft using a laser, for example. The hatch is orientated along the shaft's axis, formed proximal the balloon, for example approximately 25 cm from the distal tip of the catheter. In an alternate embodiment, no recess is formed, and a perforated edge is cut through the outer shaft, or a protruding section is formed in the outer shaft and the perforated edge is cut around its periphery. In another alternate embodiment, a guide wire port is formed by removing a portion of the outer shaft during manufacture to form a slot. The slot may be any appropriate form, for example rectangular, and large enough for a guide wire to pass through; but, it does not run the entire length of the catheter. The slot is orientated along the shaft's axis, located proximal the balloon, for example approximately 25 cm from a distal tip of the catheter.

The present invention is used as both an OTW and a RX catheter. Therefore, initially the device may be used similarly to a standard OTW catheter. In doing so, a vacuum would be pulled on the inflation port of the bifurcate hub, which is attached to the inflation lumen as described above. Pulling a vacuum would collapse the balloon and the crescent-shaped inner shaft and thus enlarge the guide wire lumen. The enlarged guide wire lumen allows the guide wire to freely move therein resulting in better trackability of the catheter through a body lumen. Of course, when the present invention is used solely as an OTW catheter, the perforated hatch need not be removed and no guide wire port would exist in the outer shaft. This arrangement accommodates better wire movement with no concern that the guide wire will exit the guide wire lumen through the guide wire port when it is not desired to do so.

Alternatively, the catheter is useable as a RX device. Again, with the balloon and inflation lumen under vacuum the catheter is threaded over the positioned guide wire. As the proximal end of the guide wire approaches the guide wire port in the outer shaft, the catheter can be orientated in order to prompt the proximal end of the guide wire to exit through the guide wire port formed in the outer shaft by removal of the perforated hatch. Further, because the present invention contains a guide wire lumen the entire length of the catheter, it is possible to remove the guide wire if required during use by simply pulling the guide wire out, whilst maintaining catheter position, and back loading a new guide wire into the guide wire hub of the bifurcate hub. From this point, the catheter is once again being used as an OTW catheter.

BRIEF DESCRIPTION OF THE DRAWINGS

The foregoing and other features and advantages of the invention will be apparent from the following, more particular description of a preferred embodiment of the invention, as illustrated in the accompanying drawings.

FIG. 2A is a detail view of portion A of the catheter of FIG. 1.

FIG. 2B is a cross-sectional view of the catheter portion of FIG. 2A taken along line 2B—2B.

FIG. 3A is a longitudinal view of another embodiment of portion A of the catheter in FIG. 1.

FIG. 3B is a cross-sectional view of the catheter portion of FIG. 3A taken along line 3B—3B.

FIG. 4A is a cross-sectional view of the catheter of FIG. 1 along line 4—4 with the inflation lumen inflated.

FIG. 4B is a cross-sectional view of the catheter of FIG. 1 along line 4—4 showing the inflation lumen collapsed.

DETAILED DESCRIPTION OF THE INVENTION

A preferred embodiment of the present invention is now described with reference to the figures, where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention.

Figure 1:
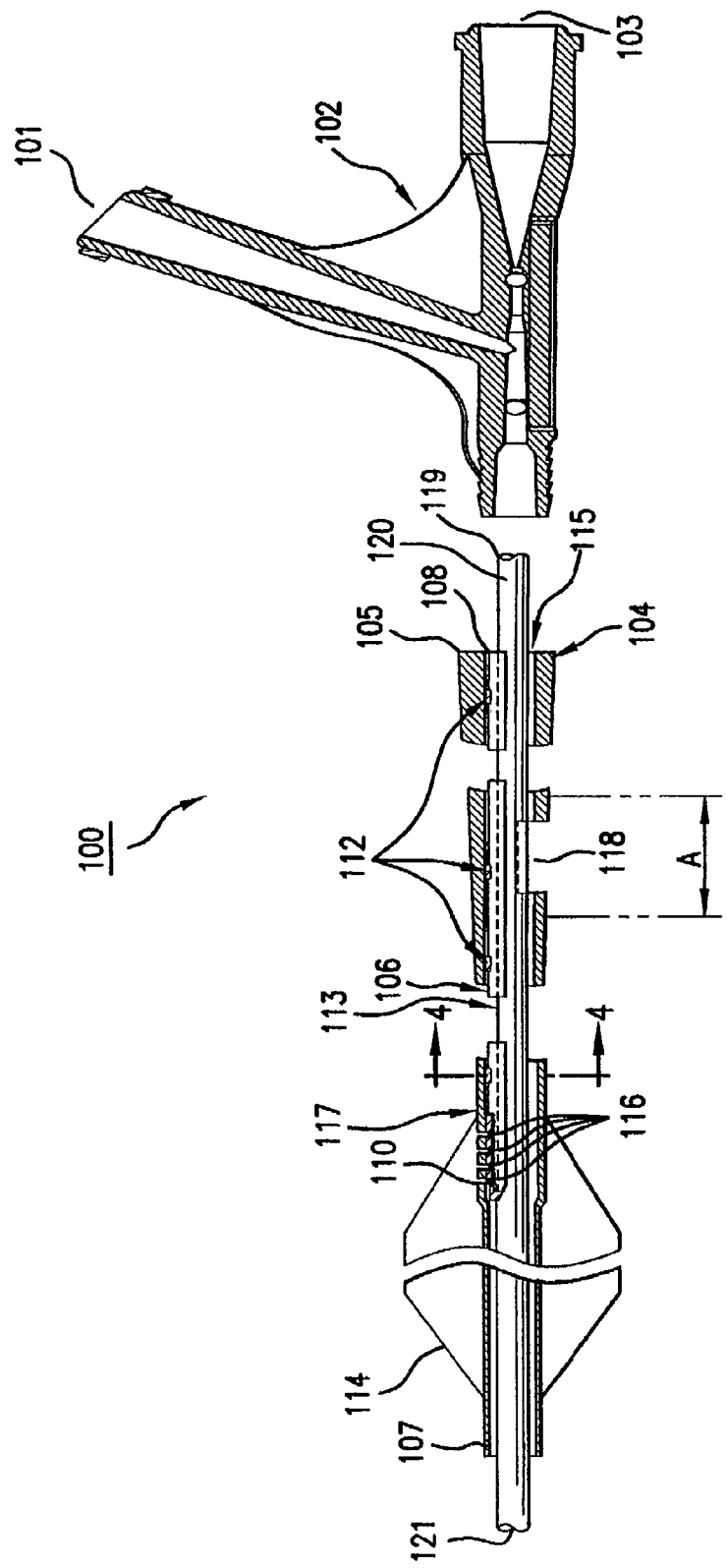
FIG. 1 is an schematic view of portions of a catheter according to the present invention.

Referring to FIG. 1, an embodiment of the convertible balloon catheter 100 of the present invention is shown. A convertible balloon catheter 100 is provided with a bifurcate hub 102, an outer shaft 104, an inner shaft 106, and an angioplasty balloon 114. Bifurcate hub 102 has an inflation hub 101 and a guide wire hub 103. Outer shaft 104 has a proximal end 105 and a distal end 107. Outer shaft 104 may be tapered from proximal end 105 to distal end 107 to allow for low profile at distal end 107. Inner shaft 106 has a proximal end 108, and a distal end 110. Tack welds 112 attach inner shaft 106 to outer shaft 104 at various points along the length of the catheter shaft.

Outer shaft 104 can be a single extrusion shaft, which may or may not be of constant profile and made of any appropriate polymeric material. Non-exhaustive examples of material for outer shaft 104 include polyethylene, Nylon, and Pebax. Inner shaft 106 is made of a relatively elastic, deformable material. Possible materials used in construction of the inner shaft are poly(ethylene terephthalate) (PET), which allows for very thin walls while withstanding ultra-high inflation pressures; Nylon, which provides a soft material; and, polyethylene, which is advantageous for its compatibility with new angioplasty techniques, such as lasers. Balloon 114 can be any appropriate shape or size, and any material, which is relatively elastic and deformable. Non-exhaustive examples of material for balloon 114 include PET, Nylon, polyethylene, and polyurethane.

Angioplasty balloon 114 is attached to an outer surface 117 of outer shaft 104 at distal end thereof. Fluid communication ports 116 are formed through inner shaft 106 and outer shaft 104 to allow fluid communication between an inflation lumen of inner shaft 106, and balloon 114. Distal end 110 of inner shaft 106 is hermetically sealed. Catheter 100 is manufactured for use with a guide wire 120. Guide wire 120 has a proximal end 119 and a distal end 121.

FIG. 2A shows a detailed view of a first embodiment of portion A of catheter 100 in a vicinity of a guide wire port 118. FIG. 2A shows outer shaft 104, inner shaft 106, tack welds 112, and guide wire 120. FIG. 2B shows a cross-sectional view of the catheter portion shown in FIG. 2A along line 2B—2B. Depicted are outer shaft 104, inner shaft 106, tack weld 112, an inflation lumen 222, a guide wire lumen 224, guide wire 120, and guide wire port 118. The figure shows one embodiment, the crescent-shaped cross section of inflation lumen 222 of inner shaft 106.

FIG. 3A shows another embodiment of portion A of catheter 100 of FIG. 1. FIG. 3A shows a hatch 326 with a plurality of peripheral perforations 328 that allow hatch 326 to be removed to form guide wire port 118. The view depicts hatch 326 recessed from the outer surface of outer shaft 104.

FIG. 3B shows a cross-sectional view of the catheter portion shown in FIG. 3A along line 3B—3B. FIG. 3B depicts hatch 326 recessed from the outer surface 117 of outer shaft 104.

Figure 3C:
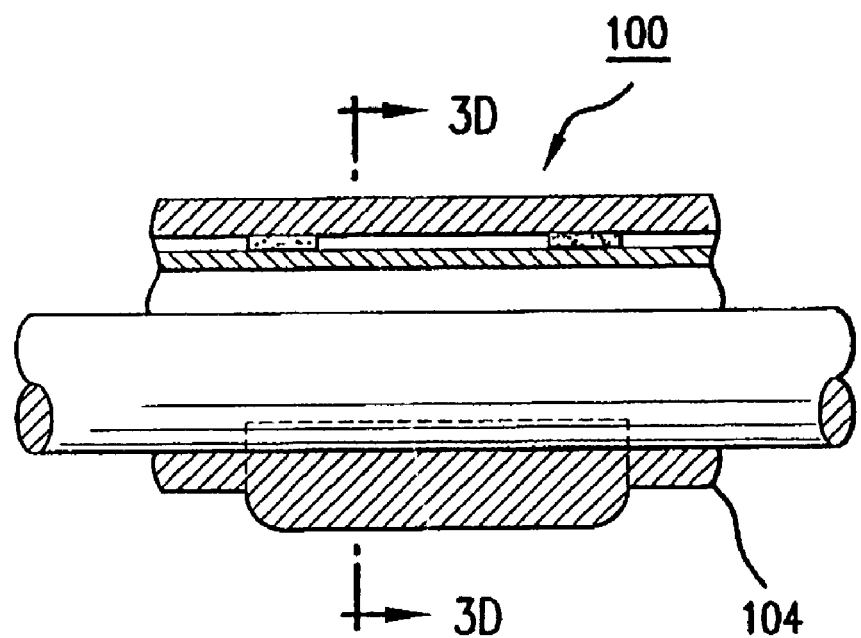
FIG. 3C is a longitudinal view of another embodiment of portion A of the catheter of FIG. 1.

FIG. 3C shows another embodiment of portion A of catheter 100 of FIG. 1. FIG. 3C shows a hatch that protrudes through the outer surface 117 of outer shaft 104.

Figure 3D:
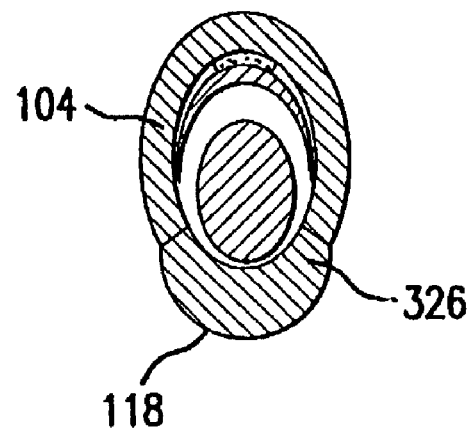
FIG. 3D is a cross-sectional view of the catheter of FIG. 3C taken along line 3D—3D.

FIG. 3D shows a cross-sectional view of the catheter portion shown in FIG. 3C along line 3D—3D. FIG. 3D depicts hatch 326 protruding from the outer surface 117 of outer shaft 104.

FIG. 4A. depicts a cross-sectional view of catheter 100 along line 4—4 in FIG. 1. FIG. 4A shows inner shaft 106 inflated. When inflated, the cross-section of inflation lumen 222 is increased in size and guide wire lumen 224 is significantly reduced in size.

FIG. 4B shows a cross-sectional view of catheter 100 along line 4—4 of FIG. 1 with inner shaft 106 collapsed showing the cross-sectional area of inflation lumen 222 decreased and cross-sectional area of guide wire lumen 224 significantly increased.

Use of the convertible balloon catheter shown in FIGS. 1–4 and described above is now briefly described. Initially, catheter 100 may be used in an over-the-wire manner. In this instance, a vacuum is pulled on inflation hub 101 of bifurcate hub 102. This collapses inner shaft 106 and increases the area of guide wire lumen 224. Guide wire 120 is positioned in the patient's coronary artery and tracked until distal end 121 is over the treatment site. Proximal end 119 of guide wire 120 is then introduced into distal end 107 of outer shaft 104 and tracked through catheter 100 until proximal end 119 of guide wire 120 clears bifurcate hub 102.

After balloon 114 has crossed the stenosis or lesion, balloon 114 can be inflated in a conventional manner by introducing a fluid through inflation lumen 222, following which, guide wire 120 and catheter 100 may be removed from the coronary artery.

Alternatively, catheter 100 may be used in the manner of a rapid exchange device. Guide wire 120 is positioned in the patient's coronary artery and tracked until distal end 121 is over the lesion. A vacuum is pulled on inflation hub 101 of bifurcate hub 102. This collapses inner shaft 106 and increases the size of guide wire lumen 224. Proximal end 119 of guide wire 120 is threaded into distal end 107 of outer shaft 104 of catheter 100. Hatch 326 is removed from outer shaft 104 thereby forming guide wire port 118. In an alternate embodiment, outer shaft 104 includes a slot therein which forms guide wire port 118. As proximal end 119 of guide wire 120 approaches guide wire port 118, catheter 100 is oriented to prompt the end of the wire to exit through guide wire port 118. At this point, proximal end 119 of guide wire 120 is external to outer shaft 104. The operator may hold guide wire 120 steady and track catheter 100 thereon to the treatment site.

Use of the device in the rapid exchange manner allows the operator to hold catheter 100 in place and remove and/or exchange guide wire 120. Guide wire 120 could be pulled out through guide wire port 118, whilst maintaining catheter position. Once guide wire 120 has been removed by the operator, a new guide wire may be back loaded into catheter 100 through guide wire hub 103 in bifurcate hub 102 and tracked to the treatment site. From this point, catheter 100 is once again being used in an over-the-wire manner.

While the invention has been particularly shown and described with reference to preferred embodiments thereof, it will be understood by those skilled in the art that various changes in form and details may be made therein without departing from the spirit and scope of the invention.

What is claimed is:

1. A balloon catheter comprising:
   a flexible outer shaft having a proximal end, a distal end, an inner surface, an outer surface, and an outer diameter;
   an inner shaft having a thin wall with an inner surface and an outer surface, wherein said inner surface of said inner shaft comprises a crescent shaped inflation lumen and wherein a guide wire lumen is formed between said outer surface of said inner shaft and said inner surface of said outer shaft; wherein said inner shaft is radially collapsible to enlarge said guide wire lumen;

a balloon mounted to said distal end of said outer shaft, wherein an interior of said balloon is in fluid communication with said inflation lumen;

a hatch disposed in said outer shaft proximal of said balloon, an outer surface of said hatch is recessed from said outer surface of said outer shaft, wherein said hatch is removable to create a guide wire port; and a bifurcate hub mounted to said proximal end of said outer shaft.

2. The balloon catheter of claim 1, wherein said outer surface of said hatch is protruding from said outer surface of said outer shaft.

* * * * *